(12) United States Patent
Denny et al.

(10) Patent No.: US 6,320,063 B1
(45) Date of Patent: Nov. 20, 2001

(54) SYNTHETIC METHOD

(75) Inventors: William Alexander Denny; Ho Huat Lee, both of Auckland (NZ)

(73) Assignee: BTG International Limited, London (GB)

(*) Notice: Subject to any disclaimer, the term of this patent is extended or adjusted under 35 U.S.C. 154(b) by 0 days.

(21) Appl. No.: 09/736,360

(22) Filed: Dec. 15, 2000

Related U.S. Application Data

(63) Continuation of application No. PCT/GB99/02337, filed on Jul. 20, 1999.

(30) Foreign Application Priority Data

Jul. 21, 1998 (GB) .................................................. 9815910

(51) Int. Cl.$^7$ .................................................. C09B 1/16
(52) U.S. Cl. .................................................. 552/247
(58) Field of Search .................................................. 552/247

(56) References Cited

FOREIGN PATENT DOCUMENTS

| 2004293 | 3/1979 | (GB) . |
| 91/05824 | 5/1991 | (WO) . |

OTHER PUBLICATIONS

Bergmann E D et al., "Preparation of 3,6,–difluorophthalic anhydride", Journal of the Chemical Society, 1194–1195 (1964).

Krapcho Paul A et al., The synthesis of 1,4–difluoro-5, 8–dihydroxyanthracene–9,10–dione and ipso substitutions of the fluorides by diamines leading to 1,4–bis[(aminoalkyl)amino]–5,8–dihydroxyanthracene–9,10–diones, Synth. Commun. 20(14), 2139–2146 (1990).

Krapcho Paul A et al., "Convenient Synthetic Routes to 1,4–Difluoroanthacene–9,10–dione", Synth. Commun. 15(10), 907–910 (1985).

Meyer A Y et al., "Planar and Nonplanar Unsaturation. Preparation, Properties and Molecular–Orbital Characterization of some Fluoro–Derivatives of Anthracene and Anthraquinone", Israel Journal of Chemistry 11(6), 791–804 (1973).

Heller A, "Preparation of 3–Fluorophthalic Anhydride", J. Org. Chem. 25, 834–835 (1960).

Caswell L R et al., "Cyclic Imides. 16. Hydroxy and Methoxy Derivatives of Aminophthalimide and Phthalhydrazide", J. Heterocyclic Chem. 32, 907–914 (1995).

O'Reilly N J et al., "Selective Hydrodechlorination of 3,4,5,6–Tetrachlorophthalic Anhydride: Preparation of 3,4, 6–Trichlorophthalic Acid" Synlett, 339–340 (1990).

Bartroli J et al., "Disubstituted Tetrahydrofurans and Dioxolanes as Patent Application Antagonists" J. Med. Chem. 34, 373–386 (1991).

*Primary Examiner*—Alton Pryor
(74) *Attorney, Agent, or Firm*—Nixon & Vanderhye

(57) ABSTRACT

A process for the preparation of the compound AQ4 of formula 3:

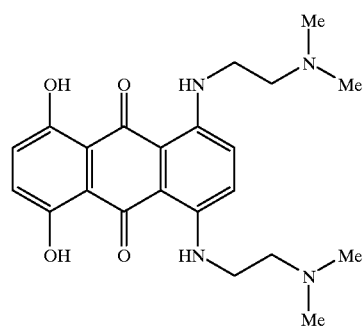

or a salt or N-oxide thereof, includes the step:

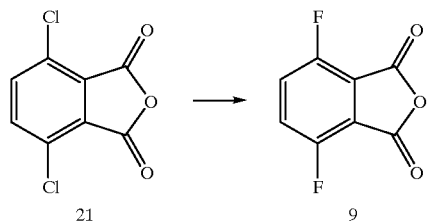

10 Claims, No Drawings

SYNTHETIC METHOD

This appl'n is a continuation of PCT/GB99/02337 filed Jul. 20, 1999.

The invention relates to a process for the preparation of AQ4 and derivatives thereof including AQ4N, a bis-bioreductive agent with of value in the treatment of cancer.

AQ4N is an anthraquinone, and would normally be synthesised by oxidation of AQ4 (3):

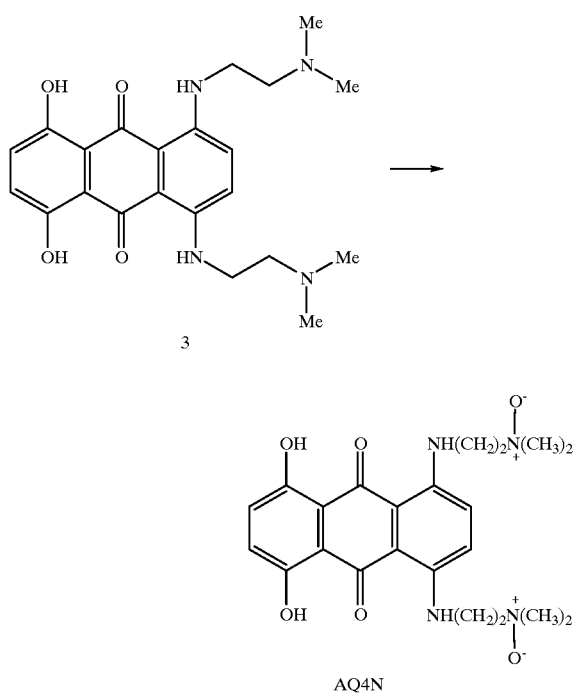

AQ4N is in fact a prodrug and the reverse reaction occurs in vivo, reductive metabolism in hypoxic cells giving the active agent, AQ4, in its protonated form. The prodrug is non-toxic, making its synthesis in large quantities desirable.

AQ4 has been prepared previously by the method of Scheme 1 (*J. Chem. Soc.* 1937, 254; *J. Med. Chem.* 1979, 22; *Synth. Comm.* 1995, 25, 1893).

Scheme 1

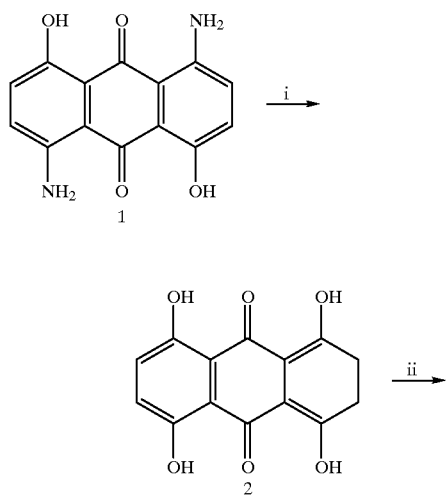

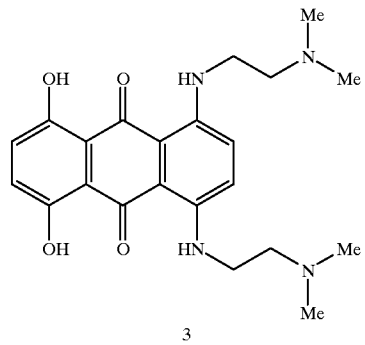

i: NaOH/Na$_2$S$_2$O$_4$/H$_2$O/70–100° C.
ii: Me$_2$N(CH$_2$)$_2$NH$_2$/EtOH/50–60° C./21 h, then air oxidation.

Alternatively, 1,8-diamino-4,5-dihydroxyanthraquinone (U.S. $14/1 g: Aldrich Chemical Co., Gillingham, England) can be substituted for 1 in Scheme 1. We have also prepared 3 by the route as shown in Scheme 1, and found that the leuco compound 2 was formed in low purity but was too unstable to be purified. Subsequent direct use of this led to impure 3, which required extensive column chromatography to obtain material pure enough to crystallise. The overall yield of 3 from 1 was 33% (of 90–97% purity) following one column/crystallisation cycle, and 25% (of 98% purity) following a second column/crystallisation cycle. The expense of the starting material 1 and the difficulty of the chromatography (requiring much time and large volumes of solvents because of the insolubility of 3) does not make this a very viable large-scale synthesis to provide compound of the purity required.

We used this route to make 3 in 5 g quantity. This took a great deal of effort, to give 3 in 25% overall yield, at ca. 97% purity (impurity profile; small amounts of several unknown products). The cost of starting material 1 (4 kg) to make 1 kg of AQ4N was approximately £5000 at catalogue prices. While the cost is perhaps acceptable, this route is not operationally suitable for large-scale synthesis.

An alternative synthesis of 3 has been reported from the 1,4-difluoro compound 4 (Scheme 2; *J. Med. Chem.* 1991, 34, 2373). We confirmed the reported results, obtaining a 78% yield of 3 (94% pure before recrystallisation, with no major impurities). This reaction is suitable for scale-up, and it seems likely that material of adequate purity could be obtained by recrystallisation. The analogous dichloro compound 5 gave only trace amounts of 3 (Scheme 2), and the protected dibenzyl ether 6 was no better, indicating that the use of 4 was mandatory in this route.

Scheme 2

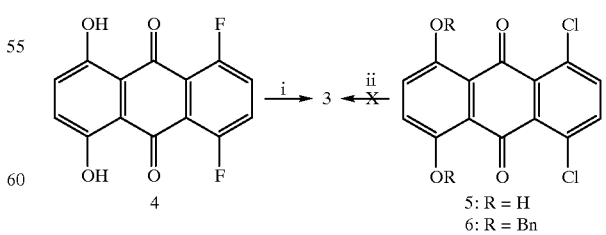

i: Me$_2$N(CH$_2$)$_2$NH$_2$/pyridine/20° C./48 h.
ii: Me$_2$N(CH$_2$)$_2$NH$_2$/various Synthesis of the key intermediate 4 was thus investigated. Successful halogen exchange has been reported (*Synth. Comm.* 1985, 15, 907) for the 1,4-dichloro-anthraquinone 7 (7→8; Scheme 3), but this was not successful with the required analogues 5 or 6 (Scheme 3).

Scheme 3

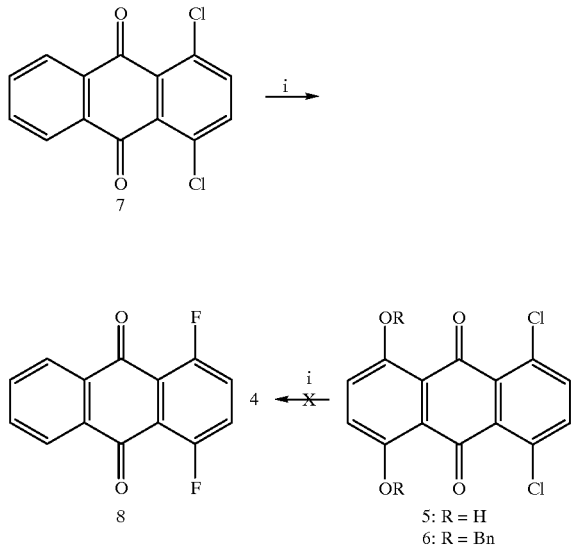

i: KF/245° C./25 h.

Another reported synthesis of 4 has been via the difluorophthalic anhydride 9 (*Synth. Comm.* 1995, 20, 2139), and we verified this synthesis, obtaining an 89% yield of pure 4 (Scheme 4).

Scheme 4

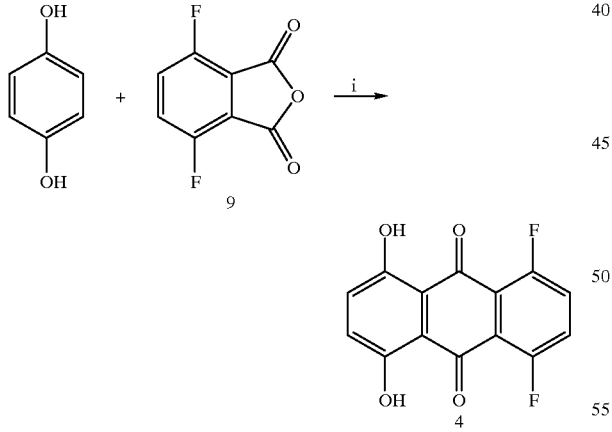

i: AlCl$_3$/220° C./1.5 h.

Operationally this is the best method, but the cost of starting material 9 (2 kg) is prohibitive (U.S. $230,000 at catalogue price, if available in this quantity). Syntheses of this also have to be considered. Two syntheses have been reported, In Scheme 5 (*Synth. Comm.* 1990, 20, 2139), the overall yield of 9 is 40% from the acid chloride 10 (U.S. $24/5 g: Aldrich Chemical Co.). The overall yield is good, but the cost of 10

Scheme 5

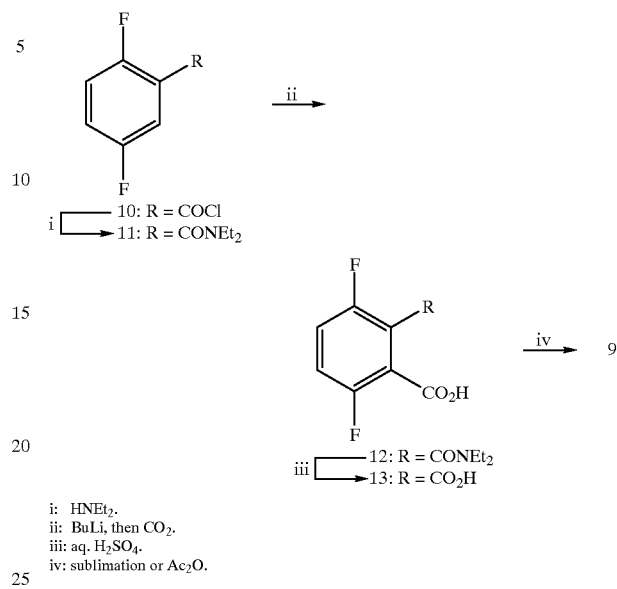

i: HNEt$_2$.
ii: BuLi, then CO$_2$.
iii: aq. H$_2$SO$_4$.
iv: sublimation or Ac$_2$O.

(while much less than 9) is still high, and the 4-step synthesis will add to costs. especially the BuLi step. Cost of staring material 10 (5 kg) is prohibitive (U.S. $24,000 at catalogue price, if available in this quantity).

Scheme 6

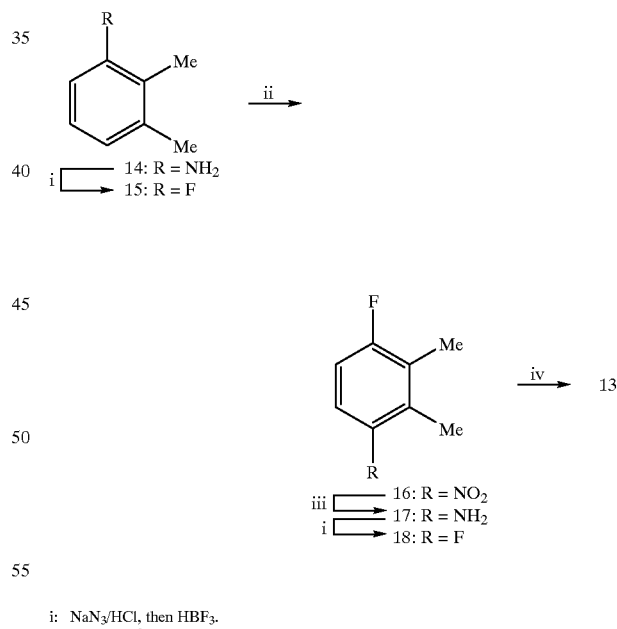

i: NaN$_3$/HCl, then HBF$_3$.
ii: HNO$_3$/-10° C.
iii: Fe/aq. NH$_4$Cl/reflux/6 h.
iv: 15% HNO$_3$/190–200° C. (autoclave)/ 3 h.

Scheme 6 outlines a synthesis from cheap 2,3-dimethylaniline 14 (U.S. $53/500 g: Aldrich Chemical Co.). Fluorination followed by nitration gave 16 (*J. Chem. Soc.* 1963, 5554). This was converted to 17 and then by a second fluorination to 18, followed by oxidation with nitric acid to the previously-mentioned 13 (see Scheme 5).

The lower cost starting material for Scheme 6 would probably be offset by the much lower overall yield reported (8%). This is largely due to a low yield (30%) in the 17→18 conversion.

A study of diverse reports (*Syn. Lett.* 1990, 339; *J. Org. Chem.* 1993, 58, 261; *Het. Chem.* 1995, 32, 907) suggests an alternative synthesis (Scheme 7).

Scheme 7

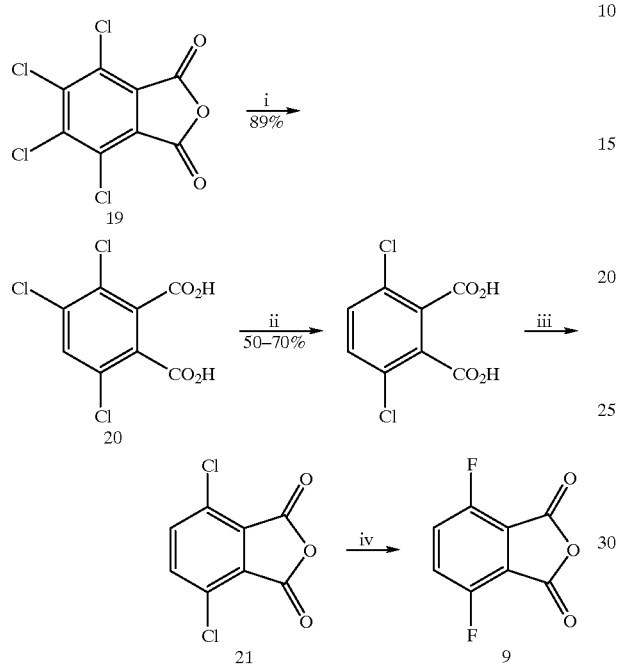

i: Zn (5 wt %)/NaOH/70–80° C./6 h.
ii: Zn (10 wt %)/NaOH/95–100° C./5 h.
iii: Toluene, distill/azeotrope.
iv: KF/NaF/250–270° C./2 h.

The tetrachlorophthalic anhydride (19) is cheap (U.S. $63/3000 g: Aldrich Chemical Co.), and can be dechlorinated in two successive reactions to give the dichlorophthalic anhydride 21 in 45–60% overall yield. The well-defined conditions listed are required to achieve clean product in each case. A single step from 19→21 does not work well, due to the differing requirements for the separate dechlorinations. The products (19, 20, 21) are not distinguishable by TLC, requiring NMR to determine purities. While 21 is also commercially available it is expensive (U.S. $59/1 g: Aldrich Chemical Co.), and it is probably cheaper to make it by the above method. The dichloro compound 21 has been reportedly converted into the desired difluoro analogue 9 in ca. 60% yield using KF (Bergmann et al.; *J. Chem. Soc.* 1964, 1194), but few details were given. However, it is difficult to repeat the reaction using the sketchy reported conditions, owing to sublimation of the anhydride 21 at 250° C. Alternative methods using solvents give only very low yields. This problem would have to be solved for this route to be viable.

Synth. Comm., 1990, 20, 2139 uses the difluorophthalic anhydride 9 but does not mention the Bergmann et al. paper (*J. Chem. Soc.* 1964, 1194). Instead, it notes "development of a practical synthesis of [3,6-difluorophthalic anhydride]". This implies that the previous Bergmann et al. method is not practical. They then develop a quite different (but longer) route to this compound (Scheme 5, above).

The same authors, in an earlier paper (*Synth. Comm.* 1985, 15, 907), do specifically reference the Bergmann et al. paper. They then go on to develop two alternative routes to the next compound in the synthesis (compound 4, above), bypassing the need to make 3,6-difluorophthalic anhydride. This again implies that the Bergmann et al. method to make this compound is not practical.

We have now solved this problem by using a nitrogen atmosphere and repeated remelting of the sublimate to obtain useful results.

Thus the present invention provides a process for the preparation of the compound AQ4 of formula 3:

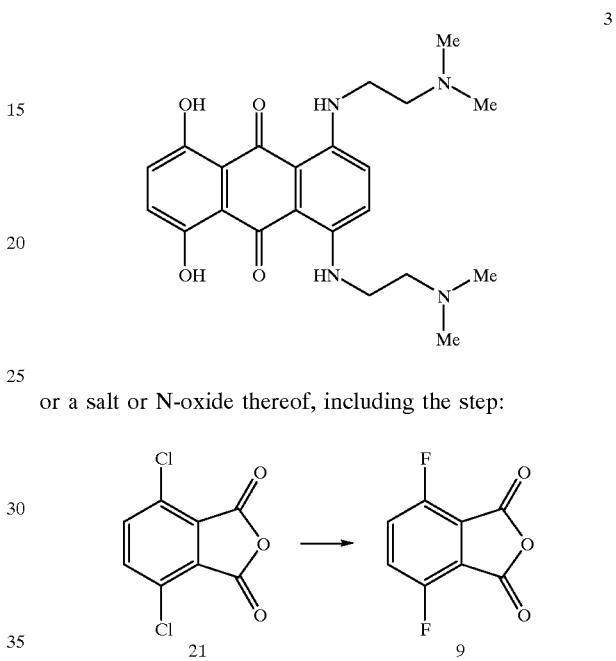

or a salt or N-oxide thereof, including the step:

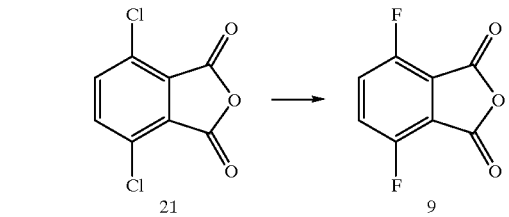

Preferably the reaction is carried out using a nitrogen atmosphere.

Any method of mixing the reaction to ensure even heating and maximum contact between the melt of 21 and the inorganic fluoride may be used. However, preferably the reaction mixture is heated to cause sublimation of solid, with frequent remelting of the sublimate back into the reaction mixture. Gentle stirring internally aids reaction.

The reaction is preferably conducted over a layer of powdered anhydrous KF and/or NaF, and more preferably a mixture of anhydrous KF and NaF. Preferably the mixture of KF and NaF contains from 10% to 60% by weight of NaF and from 90% to 40% by weight of KF, and more preferably around 17% by weight of NaF and around 83% by weight of KF.

Preferably the reaction mixture includes:

| | |
|---|---|
| 5 | parts by weight dichlorophthalic anhydride (21); |
| 10 to 25 especially around 20, | parts by weight KF; and |
| 2 to 6 especially around 4 | parts by weight NaF. |

The reaction is preferably conducted at a temperature of 260–270° C.

The above reaction step is a critical step and very dependent on conditions that were not reported by Bergmann et al.; *J. Chem. Soc.* 1964, 1194). Thus on a small scale (10 g), a bath temperature of 245–250° C. works better than 260–270° C., giving a cleaner product and a higher yield.

However, on a 100 g scale this temperature range did not work well, with the reaction only going part way. Because the reaction is heterogeneous (the compound 21 melts but the KF does not), efficient heat transfer is critical, and the margin between incomplete reaction (less than 260° C.) and rapid decomposition (greater than 270° C.) is very narrow. Something as simple as using a thick-walled flask greatly lowers yield.

We have found that using a thin-walled flask, and a mixture of KF (400 g) and NaF (80 g) for 100 g of 21 improves yields. This results in a looser reaction "cake" after the reaction is complete, allowing a more rapid removal of product by sublimation (at 140° C. to 170° C., 0.3 mm Hg). In turn this results in less decomposition during sublimation, and a purer product.

Reagent ratio is also critical; if only half the amount of KF/NaF is used, there is essentially no reaction.

The reaction may be used to prepare AQ4 (3) or its N-oxide AQ4N:

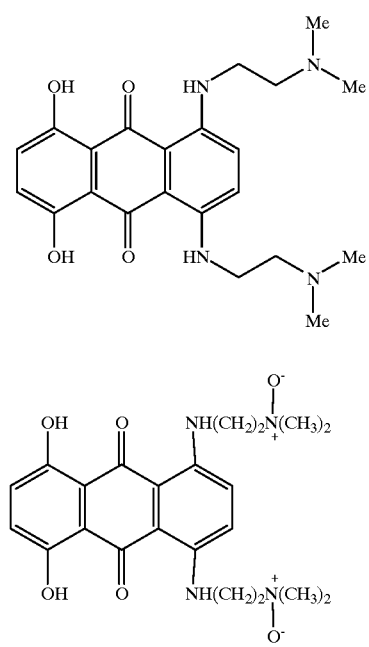

Making the intermediate 9 via Scheme 7 this way is operationally acceptable (a three-step synthesis in about 35% overall yield). Cost of starting material 19 (4 kg) is trivial (U.S. $100 at catalogue price). We believe that the best (perhaps the only economically feasible) route to AQ4N is as follows (Scheme 8). This five-step synthesis from a cheap (U.S. $63/3 kg: Aldrich Chemical Co.) and readily-available starting material requires only one straightforward filtration chromatography step (at the end, to remove a few percent of the monochloro compound 23, arising from the analogous monochloro anhydride 22).

Scheme 8

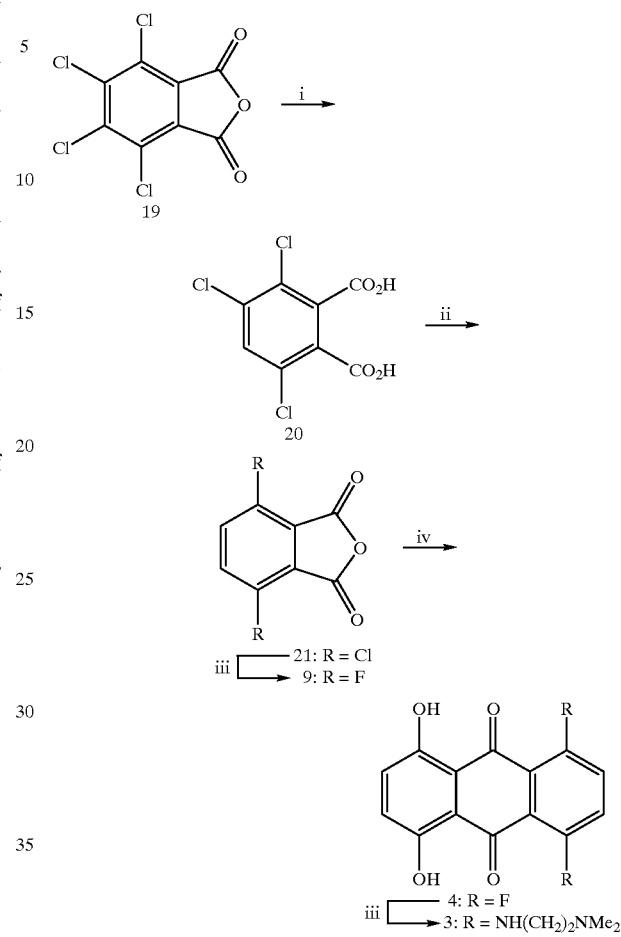

i: Zn (5 wt %)/NaOH/70–80° C./6 h.
ii: Zn (10 wt %)/NaOH/95–100° C./5 h.
iii: KF/NaF/260–270° C./2–3 h.
iv: Hydroquinone/AlCl$_3$/200±5° C./2 h.
v: N,N-dimethyethylenediamine/20° C./45 h.

This delivers AQ4 in overall 15% yield (22% on a gram/gram basis) in ≧97% purity directly off the column (containing one major unknown impurity of ca. 1%). All steps have been carried out on at least a 100 g scale, and are potentially scaleable further.

Oxidation of the AQ4 product using, for example, Davis reagent, gives the bis-N-oxide AQ4N. The route may be modified to make the mono-N-oxide 24, by limiting the degree of oxidation that occurs.

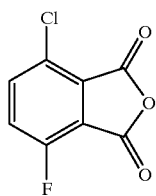

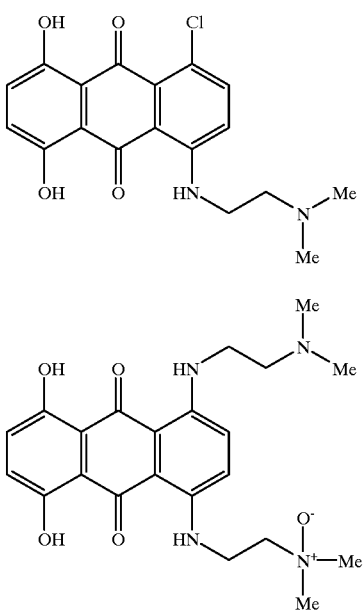

SYNTHESIS DETAILS 3,4,6-Trichlorophthalic Acid (20). This compound was prepared by modifications to the literature method of *Syn. Lett.*, 1990, 339. A mixture of 3,4,5,6-tetrachlorphthalic anhydride (19) (Aldrich Chemical Co., 100 g, 0.35 mmol) and NaOH (50.0 g, 1.25 mmol) in water (1000 mL) was stirred at 50–60° C. (bath) for 45 min under a nitrogen atmosphere. Zinc dust (70.0 g, 1.07 mmol) was then added portionwise over 10 min, and the mixture was stirred at 70–80° C. for a further 6 h. The reaction was cooled to room temperature and filtered through a bed of Celite, and the filter and residue was washed successively with 0.1N NaOH (2×100 mL) and H$_2$O (2×100 mL). The combined filtrate was acidified with conc. HCl to pH≦1, and the colourless precipitate was collected by filtration and washed with 0.1N HCl (3×100 mL). The damp solid was stirred with EtOAc (600 mL) and acidified with conc. HCl until all the solids had dissolved. The EtOAc layer was separated and the aqueous portion further extracted with the same solvent (2×100 ml, The combined EtOAc solution was dried (Na$_2$SO$_4$), filtered, and evaporated under reduced pressure give 3,4,6-trichlorophthalic acid (20) (83.5 g, 89%) as a colourless solid; m.p. (without recrystallisation) 151–153° C. (lit. m.p. 150–153° C.), $^1$H NMR identical to literature.

3,6-Dichlorophthalic Anhydride (21). This compound was prepared by modifications to the literature method of *J. Het. Chem.*, 1995, 32, 907. Zinc dust (165 g, 2.52 mmol) was added portionwise (over 15 min) to a homogenous mixture of 20 (118 g, 0.437 mmol) and NaOH (120 g) in water (1200 mL) stirred at 90° C. (bath) under a nitrogen atmosphere. The resulting heterogeneous mixture was further stirred at 95–100° C. for 5 h, then cooled to room temperature and filtered through a bed of Celite. The filter and residue was washed with water (3×100 mL), and the combined filtrate was acidified with conc. HCl (250 mL) and extracted with EtOAc (2×300 mL). The combined EtOAc solution was dried (Na$_2$SO$_4$), filtered and evaporated under reduced pressure to give crude 3,6-dichlorophthalic acid (100 g). Toluene (1000 mL) was added to this solid, and the mixture was distilled until the distillate was clear (after about 600 mL had been collected). The hot concentrate was gravity-filtered, and the residue was washed with hot toluene (3×50 mL). The combined filtrate was seeded and chilled to give 3,6-dichlorophthalic anhydride (21) as a colourless solid (67.0 g, 72%), m.p. 187–190° C. (lit. m.p. 188–191° C.). $^1$H NMR identical to literature.

3,6-Difluorophthalic Anhydride (9). This compound was prepared as reported previously without conditions in the literature (Bergmann et al.; *J. Chem. Soc.*, 1964, 1194), and well-defined conditions and operating procedures were developed. In a 1 L round-bottomed thin-wall flask was placed a layer of 21 (100 g, 0.467 mol), over a layer of powdered mixed anhydrous KF (400 g)/NaF (80 g). This packing was not disturbed, but dried in a vacuum oven at 140° C. to 170° C. at 20 mm Hg for 7 h. The flask was transferred to an oil bath such that the oil level was about 1 cm above the solid layer. The fask was evacuated again by a water pump, and then filled with nitrogen gas. The bath was then heated to 260–270° C. and held at this temperature. After about 20 min, a considerable amount of solid sublimed onto the top of the reaction flask, and the flask was lowered gently into the oil bath until the oil level reached to the neck of the flask. When all the sublimed solid melted and flowed back onto the solid layer, the flask was returned to its original level in the oil bath. This operation was repeated at about 20 min intervals, until a light brown layer of KF/NaF was observed after 2–3 h. The reaction mixture was then sublimed at 140° C. to 170° C. (3 mm Hg) in a Kugelrohr apparatus, giving a solid product that contained mainly 3,6-difluorophthalic anhydride (9) (ca. 90% by NMR) (64.8 g, 76%); m.p. (toluene) 211–214° C. (lit. m.p. 212° C. [Bergmann et al.; *J. Chem. Soc.*, 1964, 1194]; 206–207° C. [*J. Chem. Soc.*, 1963, 3475]). $^1$H NMR identical with authentic sample (Aldrich Chemical Co.).

The only significant impurity (ca. 5–10%) present in the sublimed product is considered to be the intermediate 3-chloro-6-fluorophthalic anhydride (22). However, the above material was used for the next step without ether purification.

1,4-Difluoro-5,8-dihydroxyanthracene-9,10-dione (4). This compound was prepared by modifications to the literature method of *Synth. Comm.*, 1990, 20, 2139. A mixture of the sublimed product (9) from the above reaction (100 g, 0.55 moles), hydroquinone (63.7 g, 0.58 moles), NaCl (127 g, 2.22 moles) and powdered anhydrous AlCl$_3$ (833 g, 6.26 moles) was placed in a 5 L flask equipped with a condenser. The reactants were well-mixed by shaking, then heated over 1–2 hours to 200±5° C. (bath) under a nitrogen atmosphere (there was very large gas evolution during the heating process). After a further 2 hours at 200±5° C., the melt was poured onto ice and conc. HCl (1.6 L) was added. The mixture was stirred at room temperature overnight, and the reddish brown precipitate was collected, washed with H$_2$O and dried to give crude 1,4-difluoro-5,8-dihydroxyanthracene-9,10-dione (4) (151 g, 98%), m.p. 301–304° C. (lit. m.p. 318–319° C.). This crude product was virtually insoluble in all solvents, and showed (by TLC in EtOAc/petroleum ether 1:3) only one minor impurity (probably 1-chloro-4-fluoro-5,8-dihydroxyanthracene-9,10-dione). $^1$H NMR agreed well with literature. This material was used for the next step without further purification.

1,4-Bis[[2-(dimethylamino)ethyl]amino]-5,8-dihydroxyanthracene-9,10-dione (3: AQ4). This was prepared by modifications to the literature method of *J. Med. Chem.*, 1991, 34, 373). A mixture of crude 4 (29.6 g, 107 mmol) and N,N-dimethyl-ethylenediamine (99.5 mL, 908 mmol) in pyridine (400 mL) was stirred at room temperature under nitrogen atmosphere for 45 h. The mixture was then poured into brine (1600 mL) and stirred at room temperature for 30 min. The blue precipitate was collected by filtration, washed with 1 N NH$_4$OH (1000 mL), and dried under vacuum over KOH/silica for 15 h. This crude product (21.5 g) was dissolved in CH$_2$Cl$_2$ and transferred to a silica gel flash column. The faster-running pink impurity was eluted in a gradient of MeOH (0.5, 1 and 2%) in CH$_2$Cl$_2$, and was tentatively assigned as 1-[[2-(dimethylamino)ethyl]amino]-4-chloroanthracene-9,10-dione (3: one R-Cl) (1.6 g, 4%): m.p. CH$_2$Cl$_2$) 165–167° C.; $^1$H NMR (CDCl$_3$) δ 12.97 (s, 1 H, exchangeable with D$_2$O, OH), 12.92 (s, 1 H, exchangeable with D$_2$O, OH), 10.04 (s, 1 H, exchangeable with D$_2$O, NH), 7.50 (d, J=9.5 Hz, 1 H, H-3), 7.24 (d, J=9.2 Hz, 1 H, H-6), 7.20 (d, J=9.2 Hz, 1 H, H-7), 6.98 (d, J=9.5 Hz, 1 H, H-2), 3.40 (q, J=6.3 Hz, collapse to t after D$_2$O, 2 H, NHCH$_2$), 2.67 (t, J=6.3 Hz, 2 H, NHCH$_2$CH$_2$), 2.35 (s, 6 H, NCH$_3$) Anal. (C$_{18}$H$_{17}$ClN$_2$O$_4$·½H$_2$O) C, H, N.

The blue band was excised from the column and extracted successively with CH$_2$Cl$_2$/MeOH (10:1) and CH$_2$Cl$_2$/MeOH/Et$_2$N (90:10:1). The combined extracts were filtered and evaporated to give 1,4-bis[[2-(dimethylamino)ethyl]amino]-5,8-dihydroxyanthracene-9,10-dione (AQ4; 3) (17.9 g, 41%): m.p. 240–242° C. (without recrystallisation) (lit. m.p. 236–238° C.). $^1$H NMR identical with the authentic sample. When the above reaction was repeated using 100 g of 4 for 48 h, the yield of 3 was 36%.

1,4-Bis[[2-(dimethylamino)ethyl]amino]-5,8-dihydroxyanthracene-9,10-dione bis-N-oxide (AQ4N). A stirred solution of 3 (17.75 g, 43.1 mmol) in CH$_2$Cl$_2$/MeOH (5:1) (600 mL) was treated dropwise over 30 min with a solution of 2-benzenesulfonyl-3-phenyloxaziridine (Davis reagent: *J. Org. Chem.* 1992, 47, 1775) (25.7 g, 98.2 mmol) in CH$_2$Cl$_2$ (200 mL). After addition, the mixture was stirred at 20° C. in the dark for a further 90 min. It was then concentrated under reduced pressure at 24–26° C. (bath temperature) to ca. 100–200 mL, and then diluted successively with EtOAc (400 mL) and petroleum ether (400 mL). The homogeneous mixture was stirred at 20° C. for 15 min, then kept at −10° C. for 2 h. The blue precipitate was collected by filtration, washed with EtOAc/petroleum ether (1:1; 4×100 mL), and suctioned dry. It was then dissolved in MeOH (200 mL) and the solution was treated with anhydrous HCl gas until it remained acidic (pH ca. 2). After storing at −10° C. overnight, the precipitate was collected by filtration and washed successively with MeOH/EtOAc (1:1; 5×30 mL) and EtOAc (2×30 mL), and dried under vacuum to give AQ4N dihydrochloride (17.7 g, 80%), m.p. 243–245° C. HPLC shows a purity of ca. 98.5%, with ca. 0.5% of the mono-N-oxide 24 (a decomposition product) and ca. 1% of an unknown impurity.

Notes

1. AQ4N was found to be somewhat unstable in MeOH solution at 20° C. in daylight, decomposing slowly to numerous other products.

2. The solid dihydrochloride should be stored in a sealed container in a cold dark place (preferably a freezer). Before opening such containers they should be allowed to warm to room temperature, since the dihydrochloride (and AQ4N) absorb moisture particularly rapidly when cold.

What is claimed is:

1. A process for the preparation of the compound AQ4 of formula 3:

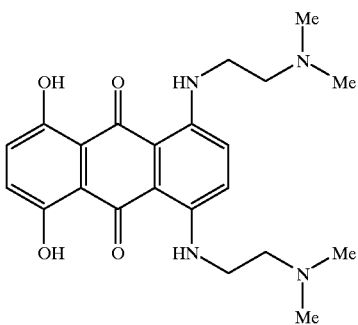

or a salt or N-oxide thereof, including the step:

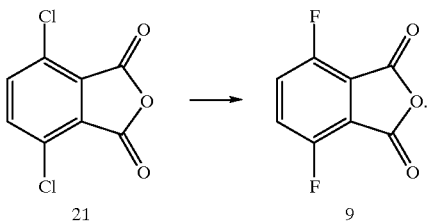

2. A process as claimed in claim 1 in which the step of converting the compound of formula 21 to the compound of formula 9 is carried out using a nitrogen atmosphere.

3. A process as claimed in claim 1 in which the step of converting the compound of formula 21 to the compound of formula 9 is carried out by heating to cause sublimation of solid, with frequent remelting of the sublimate.

4. A process as claimed in claim 1 in which the step is conducted over a layer of powdered anhydrous KF and/or NaF.

5. A process as claimed in claim 4 in which the step is conducted over a mixture of anhydrous KF and NaF.

6. A process as claimed in claim 5 in which the mixture of KF and NaF contains from 10% to 60% by weight of NaF and from 90% to 40% by weight of KF.

7. A process as claimed in claim 6 in which the mixture of KF and NaF contains around 17% by weight of NaF and around 83% by weight of KF.

8. A process as claimed in claim 5 in which the compound of formula 21, KF, and NaF are present in the following amounts:

| | | |
|---|---|---|
| 5 | parts by weight | dichlorophthalic anhydride (21); |
| 10 to 25 | parts by weight | KF; and |
| 2 to 6 | parts by weight | NaF. |

9. A process as claimed in claim 5 in which the compound of formula 21, KF, and NaF are present in the following amounts:

| | | |
|---|---|---|
| 5 | parts by weight | dichlorophthalic anhydride (21); |
| around 20 | parts by weight | KF; and |
| around 4 | parts by weight | NaF. |

10. A process as claimed in claim 1 in which the step of converting the compound of formula 21 to the compound of formula 9 is conducted at a temperature of 260–270° C.

* * * * *